(12) United States Patent
Borsook (10) Patent No.: US 7,196,071 B2
(45) Date of Patent: Mar. 27, 2007

(54) METHODS OF DECREASING OR PREVENTING PAIN USING SPICAMYCIN DERIVATIVES

(75) Inventor: David Borsook, Concord, MA (US)

(73) Assignee: The General Hospital Corporation, Boston, MA (US)

( * ) Notice: Subject to any disclaimer, the term of this patent is extended or adjusted under 35 U.S.C. 154(b) by 286 days.

(21) Appl. No.: 10/380,354

(22) PCT Filed: Sep. 20, 2001

(86) PCT No.: PCT/US01/29371

§ 371 (c)(1),
(2), (4) Date: Sep. 5, 2003

(87) PCT Pub. No.: WO02/24146

PCT Pub. Date: Mar. 28, 2002

(65) Prior Publication Data

US 2004/0038927 A1   Feb. 26, 2004

Related U.S. Application Data

(60) Provisional application No. 60/234,382, filed on Sep. 20, 2000.

(51) Int. Cl.
*A61K 31/70*   (2006.01)

(52) U.S. Cl. ............................ 514/45; 514/46; 536/27.6

(58) Field of Classification Search .................. 514/45, 514/46; 536/27.6
See application file for complete search history.

(56) References Cited

U.S. PATENT DOCUMENTS 5,252,463 A   10/1993   Nelson et al.
5,905,069 A *  5/1999   Borsook et al. .............. 514/45
6,087,091 A    7/2000   Justice et al.

FOREIGN PATENT DOCUMENTS

EP   0525479 A1   2/1993

OTHER PUBLICATIONS

Vilassova N. et al., "The Effects of KRN5500, a Spicamycin derivative, on Neuropathic and Nociceptive Pain Models in Rats.", *Database PubMed, US National Library of Medicine*, No. 11004056, Abstract; 2000.
Supplementary European Search Report for EP01971222 mailed Sep. 12, 2005.
Kamishohara et al., "Antitumor activity of a spicamycin derivative, KRN5500, and its active metabolite in tumor cells," Oncol Res 1994; 6:383-90.

* cited by examiner

*Primary Examiner*—Shaojia Anna Jiang
*Assistant Examiner*—Michael C. Henry
(74) *Attorney, Agent, or Firm*—Myers Bigel Sibley & Sajovec (57) ABSTRACT

Methods of providing pain relief by administering a water-soluble derivative of spicamycin. Methods of using pain mediation agents are also provided.

37 Claims, 2 Drawing Sheets

METHODS OF DECREASING OR PREVENTING PAIN USING SPICAMYCIN DERIVATIVES

CROSS-REFERENCE TO RELATED APPLICATIONS

This application claims the benefit of U.S. provisional application 60/234,382, filed Sep. 20, 2000.

BACKGROUND OF THE INVENTION

Spicamycin (SPM) is an antitumor antibiotic produced by the bacterium Streptomyces alanosinicus is 879-MT$_3$ (Hayakawa et al., Agric. Biol. Chem. 49:2685–2691, 1985). Spicamycin and its derivatives are also used for pain relief (U.S. Pat. No. 5,905,069). Naturally occurring SPM has the following general structure, varying solely in the fatty acid moiety:

Formula I: Spicamycin

Synthetic variants of spicamycin and their use as an antitumor agent are described in Otake et al., U.S. Pat. Nos. 5,461,036 and 5,631,238.

SUMMARY OF THE INVENTION

The invention is based on the unexpected discovery that substantial removal of the fatty acid moiety in a subclass of spicamycin derivatives results in drugs especially useful for the treatment of pain. This subclass of spicamycin derivatives exhibit increased water-solubility relative to fatty acid-containing derivatives, and are therefore more amenable to formulations suitable for human administration (e.g., formulations containing an aqueous physiological buffer). In addition, the potential toxicity of pharmaceutical formulations containing this subclass of spicamycin derivatives can be reduced because no toxic lipophilic carriers are needed in order to solubilize the active ingredients.

Thus, the invention features a method of providing pain relief by identifying a subject (e.g., a mammal, such as a human, dog, cat, or horse) in need of pain relief, and administering to the subject an amount of a compound of Formula II effective to provide significant pain relief in the subject.

Formula II $R_1$ and $R_2$ are different from each other and represent —H or —OH, and R represents (1) a substituted or unsubstituted alkyl having one or two carbon atoms (i.e., no more than two carbon atoms), or (2) —H. For example, R can contain an amino group (e.g., a primary amino group), a carbonyl group or both. When R is —COCH$_2$NH$_2$, $R_1$ is —H, and $R_2$ is —OH, the compound is known as 4'-N-glycyl spicamycin amino nucleoside (SAN-Gly). When R is —H, the compound is known as SAN. See, e.g., Kamishohara et al., Oncology Res. 6:383–390, 1994. A salt of the compound of Formula II can also be used in the methods of the invention.

The compounds (and salts thereof) of Formula II useful in the methods herein also are those where $R_1$ and $R_2$ are independently H or OH, wherein $R_1$ and $R_2$ are not simultaneously the same and:

Each R group can independently be an H or alkyl group having 1 to 5 (e.g., 1 to 2, 1 to 3, 1 to 4) carbon atoms substituted with 1 to 3 independent $R^3$ or $R^4$;

Each $R^3$ is independently heterocyclyl or heteroaryl, either optionally substituted with 1–3 independent $R^5$;

Each $R^4$ is independently halogen, oxygen, sulfur, CF$_3$, SR$^6$, OR$^6$, OC(O)R$^6$, NR$^6$R$^6$, NR$^6$R$^7$, COOR$^6$, C(O)R$^6$, or C(O)NR$^6$R$^6$;

Each $R^5$ is independently C1–C10 alkyl; halo; haloalkyl; SR$^6$; OR$^6$; NR$^6$R$^6$; COOR$^6$; NO$_2$; CN; C(O)R$^6$; C(O)NR$^6$R$^6$; OC(O)R$^6$; S(O)$_2$R$^6$; S(O)$_2$NR$^6$R$^6$; NR$^6$C(O)NR$^6$R$^6$; NR$^6$C(O)R$^6$; NR$^6$(COOR$^6$); NR$^6$C(O)R$^8$; NR$^6$S(O)$_2$NR$^6$R$^6$; NR$^6$S(O)$_2$R$^6$; NR$^6$S(O)$_2$R$^8$; or C1–C10 alkyl substituted with $R^4$ or $R^8$;

Each $R^6$ is independently H, C1–C10 alkyl; C2–C10 alkenyl; C2–C10 alkynyl; C3–C10 cycloalkyl; $R^8$; or C1–C10 alkyl substituted with $R^8$;

Each $R^7$ is independently COOR$^9$, C(O) NR$^9$R$^9$, S(O)$_2$R$^9$; or S(O)$_2$NR$^9$R$^9$;

Each $R^8$ is independently aryl, heteroaryl, or heterocyclyl;

Each $R^9$ is independently H, C1–C10 alkyl, aryl, heteroaryl, or heterocyclyl.

The term "alkyl" denotes a straight or branched hydrocarbon chain containing carbon atoms or cyclic hydrocarbon moieties. These alkyl groups may also contain one or more double bonds or triple bonds. By "substituted alkyl" is meant an alkyl in which an atom of the alkyl is substituted with, for example, a carbon, nitrogen, sulfur, oxygen, or halogen atom, or alternatively a nitrogen, sulfur, oxygen, or halogen atom.

Examples of substituents that can be attached to any atom of the alkyl group in a "substituted alkyl" include heterocyclyl groups; heteroaryl groups, amino groups, amido groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group) and sulfur (e.g. a thiocarbonyl group). Substituents also include any chemical functional group that imparts improved water-solubility to the molecule (e.g., carboxylic acid, carboxylic ester, carboxamido, morpholino, piperazinyl, imidazolyl, thiomorpholino, or tetrazolyl groups; both unsubstituted and substituted).

The terms "halo" and "halogen" refer to any radical of fluorine, chlorine, bromine or iodine. The terms "ring" and "ring system" refer to a ring comprising the delineated number of atoms, said atoms being carbon or, where indicated, a heteroatom such as nitrogen, oxygen or sulfur. The ring itself, as well as any substituents thereon, may be attached at any atom that allows a stable compound to be formed.

The term "aryl" refers to a 6-carbon monocyclic or 10-carbon bicyclic aromatic ring system wherein 0, 1, 2 or 3 atoms of each ring may be substituted by a substituent. Examples of aryl groups include phenyl, naphthyl and the like.

The term "heteroaryl" refers to an aromatic 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, wherein 0, 1, 2 or 3 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, wherein 0, 1, 2 or 3 atoms of each ring may be substituted by a substituent. Examples of heterocyclyl groups include piperizinyl, pyrrolidinyl, dioxanyl, morpholinyl, tetrahydrofuranyl, and the like.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject or antiseptic, wound dressing impregnation, sterilizant, or disinfectant applications).

A "subject in need of pain relief" does not necessarily experience pain currently, and "pain relief" includes less than 100% reduction in pain. For example, the invention can be used to treat a mammal, including a human patient, a dog, a cat, or a horse, for neuropathic pain attributable to any cause, e.g., postherpetic neuralgia, phantom or amputation stump pain, diabetic neuropathy, acquired immune deficiency syndrome neuropathy, back pain, and visceral pain (e.g., chronic pancreatitis). By "neuropathic pain" is meant pain arising from injury to or disturbance of the peripheral nervous system.

The compound can be administered locally or systemically, e.g., via an implant (for slow release, for example) or by intravenous bolus injection or infusion. An "implant" is any device residing in a tissue deeper than the skin, in which the device produces a regulated or continuous release of a compound. Such devices are well known in the art of drug delivery (see, e.g., U.S. Pat. No. 6,013,853). For example, a compound of Formula II can be prepared with carriers that will protect the compound against rapid elimination from the body, such as a controlled release formulation, including microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. The amount of compound administered at one time can be about 1 ng to 4 $mg/m^2$ body surface area (e.g., 80 ng to 1 $mg/m^2$ body surface area), and the compound can be formulated in an aqueous solution that optionally contains pharmaceutically acceptable carriers. Other suitable dosages include about 1 to 1000 mg/kg body weight (e.g., about 10 to 500, or about 100 mg/kg body weight).

Treatment in accordance with the invention produces relief of pain in patients whose current pain is resistant to other methods of pain relief, such as using opioid drugs. The invention can also be used in anticipation of pain to prevent pain.

The invention further relates to methods of selectively inhibiting, treating, or preventing neuropathic pain selectively over acute nociceptive pain comprising identifying a subject in need of pain relief, and administering a compound (or composition) of any of the formulae delineated herein, including those of Formula II. In another aspect, the method involves selectively inhibiting, treating, or preventing neuropathic pain selectively over nociceptive pain comprising identifying a subject in need of pain relief, and administering a compound (or composition) of any of the formulae delineated herein. In one aspect of these methods, selectively refers to inhibiting neuropathic pain to a greater extent than nociceptive pain. In another aspect of these methods, selectively refers to inhibiting neuropathic pain at least 50% more (e.g., >100% more, >200% more, 500% more) than nociceptive pain as determined by standard pain models, including those delineated in Borsook et al., U.S. Pat. No. 5,905,069 (and references cited therein), issued May 18, 1999, and Abdi et al., Anesth. Analg. 91, 955–999 (2000).

The invention also relates to methods of assessing, identifying, or validating genes (or polypeptides encoded by those genes) as receptors involved in pain mediation, including neuropathic pain treatment. The methods comprise contacting a compound of any of the formulae herein with a test polypeptide and measuring the binding affinity of the compound and test polypeptide. Those polypeptides (and the genes encoding them) having a greater affinity for the compound are candidates having a greater likelihood of being directly involved in pain mediation, particularly neuropathic pain mediation. As such, they would be interesting targets for research and development studies for new mechanisms of pain mediation and for targets of inhibition by ligands (e.g., peptide or small molecule drugs) for treatment or prevention of pain. The analysis of the binding affinity of the compounds and receptors can be performed using assays, methods, and techniques known in the drug screening/design, genomics, and medicinal chemistry arts, including labeling (radiolabel, fluorescence) studies for detection of compound, target, or other ligand mediating a known peptide-ligand interaction, or can involve an indirect readout (e.g., measuring presence of a marker whose release or formation is dependent upon the binding interaction of the compound and test polypeptide).

The invention further relates to methods of assessing the efficacy of potential pain drugs (e.g., peptides, chemical entities, small molecules). Because the compounds of the formulae herein are effective in mediating neuropathic pain, they are also useful as "standards" by which potential new pain drugs can be assessed. Such methods comprise evaluating a test compound (e.g., potential pain drug) against a compound of any the formulae herein (i.e., a standard), including a compound of Formula II, by subjecting the test compound and the compound of any of the formulae herein to a subject or medium (e.g., patient, animal model, cell culture, in vitro assay) that provides measure or assessment of the effectiveness of the test compound and the compound of any of the formulae herein in mediating pain or modulating the mechanism of pain. The method can further comprise evaluating the results of the compound testing to assess the effectiveness of the test compound as a pain drug. The measuring or assessing of the effectiveness of the compounds in these methods can be performed by any number of appropriate techniques and protocols known in the art and readily available.

The invention also relates to methods of identifying new genes, receptors, or peptides that are involved in mediation of pain. These methods involve use of the compounds of any of the formulae herein, including those of Formula II, to investigate metabolic effects induced by the compounds, including effects involved in pain mediation. Such methods comprise administering the compounds of any of the formulae herein to a subject or medium (e.g., patient, animal model, cell culture, in vitro assay, tissue), collecting tissue from the subject or medium (e.g., dorsal root ganglion, nerve tissue, spinal cord tissue, or central nervous system (CNS) tissue), and evaluating the tissue for effects (e.g., identifying and/or quantifying: induction, suppression, indirect responses, marker production) of known or novel genes, receptors, or peptides. The known or novel genes, receptors, or peptides are interesting targets for new drugs to mediate pain, and provide new information and novel targets for new methods of pain mediation, treatment, or prevention. The evaluation in these methods can be performed using any number of appropriate techniques and protocols known in the art and readily available for measuring, detecting, and identifying genes, receptors, or peptides.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention relates to methods of decreasing or preventing pain by administering to a subject a water-soluble spicamycin derivative (Formula II) in an amount sufficient to decrease or prevent the pain. Accordingly, the compound of the present invention can be administered via any appropriate route, e.g. intravenously, intraarterially, topically, nasally, via inhalation into the lungs, intraperitoneally, intrapleurally, orally, subcutaneously, intramuscularly, sublingually, intraepidermally, vaginally, or rectally. The compound can be formulated as a solution, suspension, suppository, tablet, granules, powder, capsules, ointment, or cream. A variety of additives can be added to these formulations, such as a solvent (e.g., water or physiological saline), solubilizing agent (e.g., ethanol, Polysorbates, or Cremophor EL7®), agent for achieving isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogels, or polyoxyethylene hardened castor oils). If suitable, the following compounds can also be added: glycerin, dimethylacetamide, sodium lactate, a surfactant, or a basic substance such as sodium hydroxide, ethylenediamine, ethanolamine, sodium bicarbonate, arginine, meglumine, or trisaminomethane. As discussed above, organic solvents (e.g., ethanol) are not required for pharmaceutical formulations containing compounds of Formula II. However, the solubilizing agents and organic materials listed above can be used if a hydrophobic material (e.g., a second analgesic) is included in the formulation, or if the pharmacokinetic characteristic of the formulation is to be modulated. Pharmaceutical preparations such as solutions, tablets, granules, or capsules can be formed with these components or the like.

The dose of the compound of the present invention is determined in consideration of the results of animal experiments and various conditions. For example, any candidate compound for pain relief can be tested in the animal models described in the example below. More specific doses obviously vary depending on the administration method, the condition of the subject such as age, body weight, sex, sensitivity, food eaten, dosage intervals, medicines administered in combination, and the source, seriousness, and degree of pain. The optimal dose and the administration frequency under a given condition must be determined by the appropriate dosage test of a medical specialist based on the aforementioned guide.

Water-soluble, non-toxic, or less toxic derivatives of spicamycin, such as SAN and SAN-Gly, can be prepared using methods known in the art. For example, general synthetic strategies are described in U.S. Pat. Nos. 5,461,036 and 5,631,238. These strategies can be adapted to attach any R group containing one or two carbons onto a sugar group, as shown in Formula II. A specific semi-synthetic strategy for preparing SAN and SAN-Gly is described in Kamishohara et al., J. Antibiotics 46:1439–1446, 1993; Kamishohara et al., Oncology Res. 6:383–390, 1994; and U.S. Pat. Nos. 5,461,036 and 5,631,238. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and respective subsequent editions thereof.

The compounds of this invention include all salt forms thereof. Examples of such salts include those derived from pharmaceutically acceptable inorganic and organic acids and bases. Examples of suitable acid salts include acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium, potassium), alkaline earth metal (e.g., magnesium), ammonium and N-(alkyl)$_4^+$ salts. Compounds of the formulae herein include those having quaternization of any basic nitrogen-containing group therein. The compounds of this invention may contain one or more asymmetric centers and thus occur as racemates and racemic mixtures, single enantiomers; individual diastereomers and diastereomeric mixtures. All such isomeric forms of these compounds are expressly included in the present invention.

Neuropathic pain is pain derived from a lesion or disorder of the peripheral nervous system (reviewed in Woolf, Acta Neurochir. 58:125–130, 1993, and Bennett, Neuropathic Pain. In: Textbook of Pain, P. D. Wall and R. Malzack, eds., 201–224, Churchill Livingstone, Edinburgh (1994)). Patients with neuropathic pain typically present with a characteristic set of sensory disorders independent of the cause, including a constant scalding or burning pain, a partial loss of sensitivity, tactile or cold allodynia, or hyperpathia to repeated stimulation. Peripheral neuropathic pain includes a number of diverse conditions, the commonest of which are trigeminal neuralgia, postherpetic neuralgia, painful diabetic neurophathy, and the reflex sympathetic dystrophies including causalgia, mononeuropathies, and peripheral nerve injury.

Nociceptive pain is pain caused by an injury or disease outside the nervous system. It is often an on-going dull ache or pressure, rather than the sharper, trauma-like pain more characteristic of neuropathic pain. Examples of nociceptive pain include pain from cancer or arthritis, sprains, bone fractures, burns, bumps, bruises. With acute pain, the severity of pain directly correlates to the level of tissue damage. This provides a protective reflex, such as the reflex to move one's hand immediately if upon touching a-sharp or hot object. This type of pain is a symptom of injured or diseased tissue, so that when the underlying problem is cured the pain goes away. In chronic pain, the pain differs from acute pain as it does not serve a protective or other biological function. Rather, the nerves continue to send pain messages to the brain even though there is no continuing tissue damage.

Due to the differences in the mechanism and types of pain, it can be advantageous to selectively treat or prevent neuropathic pain selectively over nociceptive pain. In other instances, the pain or pain symptoms can be a combination of both neuropathic and nociceptive, in those instances treatment of both types of pain can be appropriate.

Few non-surgical alternatives exist for a patient with a disabling pain resistant to opioid drugs. The methods of this invention provide alternative water-soluble pain relievers to such patients. Increased water solubility can increase absorption into the systemic circulation when administered orally to a subject, thereby increasing bioavailability of a drug.

In addition, water-soluble derivatives of spicamycin, such as SAN-Gly, are less cytotoxic than water-insoluble derivatives of spicamycin, such as KRN5500 (Kamishohara et al., Oncology Res. 6:383–390, 1994). This implies that water-soluble derivatives of spicamycin are safer for patients receiving repetitive administrations, as may be required for treating chronic pain.

The invention also contemplates combination formulations containing a water-soluble derivative of spicamycin and a second analgesic or drug, such as an anti-inflammatory agent (e.g., aspirin, acetaminophen, ibuprofen, naproxen, diclofenac, celecoxib, NSAIDS, COX-1 inhibitors, COX-2 inhibitors, steroids, steroid derivatives, glucocorticoids).

Without further elaboration, it is believed that one skilled in the art can, based on the above disclosure and the description below, utilize the present invention to its fullest extent. The following example is to be construed as merely illustrative of how one skilled in the art can practice the invention, and is not limitative of the remainder of the disclosure in any way. All patents and publications cited in this disclosure are hereby incorporated by reference.

EXAMPLE 1

To determine whether relatively water-soluble, less toxic spicamycin derivatives are useful for pain relief, the compound SAN-Gly was semi-synthetically prepared as described in U.S. Pat. No. 5,631,238. SAN-Gly was then formulated in saline.

Male Sprague-Dawley rats (Charles River Laboratories) weighing 150–200 g were used to evaluate the analgesic properties of the SAN-Gly formulation. The animals were housed in groups of three in plastic cages with soft bedding and under a 12 hour light/dark cycle. Food and water were available ad libitum. After one week of acclimatization to the laboratory conditions, all animals were tested to establish a baseline mechanical allodynia.

Since different animal models of pain can provide different experimental results, SAN-Gly was tested using two rat models. All experiments were performed in a single-blinded fashion, i.e., the experimenter was not aware of which rats received the control saline and which rats received the SAN-Gly formulation.

One rat model used was based on an experimentally produced segmental spinal nerve injury (Kim et al., Pain 50:355–363, 1992). One week after the acclimatization to laboratory conditions, baseline measurements were recorded and surgery was performed as described in Kim et al., supra. Rats were anesthetized with halothane in oxygen and placed in a prone position. A midline skin incision at L4–S2 was made, and paraspinal muscles were separated from the spinous processes in the L4–S2 region. The left L5 and L6 spinal nerves were identified and tightly ligated with 6-O silk thread. The wound was then closed. At the end of surgery, anesthesia was discontinued, and the animals were returned to their cages with food pellets and water ad libitum. The animals recovered from anesthesia within approximately 10 minutes.

The rats were allowed to recover from surgery for at least a week. Ten to twelve days after surgery, animals were tested for allodynia by monitoring hypersensitivity to pinprick with von Frey filaments (VFF). The animals were placed on a mesh floor and covered by a transparent plastic box open at the bottom. Calibrated VFF (3.61, 3.84, 4.08, 4.31, 4.56, 4.74, 4.93, and 5.16) were applied to the plantar skin of the left hindpaw using the up-down method and a 50% foot withdrawal (paw flinching) as the pain threshold. Each VFF was tested by inserting it from below the rat and through the mesh floor, and applying it to the second, third, and fourth digits of the foot until the filament just bent (Chaplan et al., J. Neurosci. Methods 53:55–63, 1994). A trial consisted of four repetitive VFF applications (at a frequency of one per 10–15 seconds). Rats were then separated into two groups, one receiving saline and the other receiving the SAN-Gly formulation (100 mg/kg body weight; single bolus in the tail vein). Both groups were then monitored for allodynia at various time points after surgery.

The other rat model was based on an experimentally induced chronic constriction nerve injury (Bennett et al., Pain 33:87–107, 1988). Peripheral mononeurophathy was produced in rats as described in Bennett et al., supra. Surgery was conducted on rats under halothane anesthesia to expose the common sciatic nerve. Then loose constrictive ligatures were placed around the nerve, the wound closed, and the animals allowed to recover for at least a week. Animals were then tested for allodynia, separated into two groups, and retested as described above.

Figure 1:
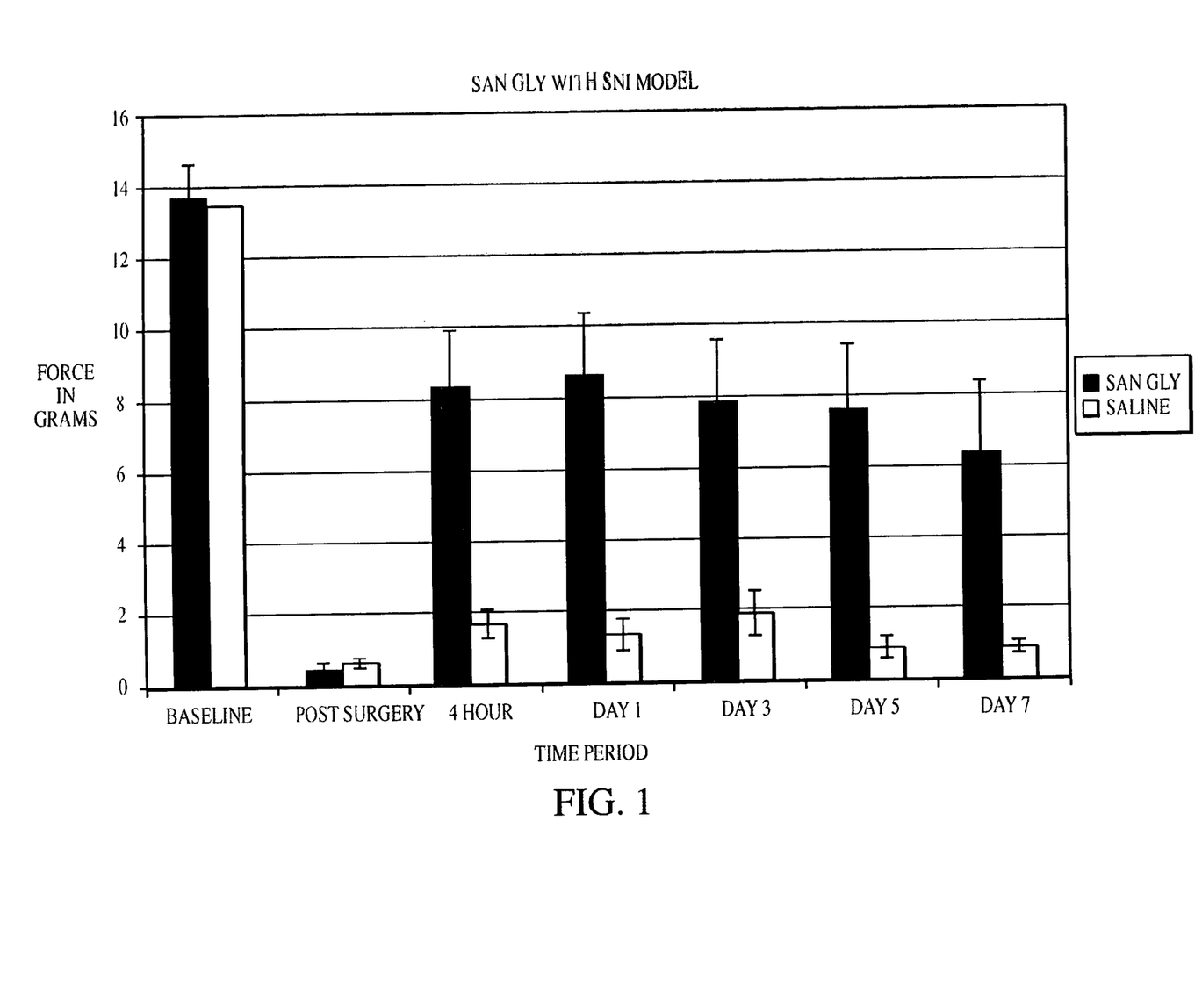
FIG. 1 is a bar graph of force in grams (high force correlates with high pain threshold) versus time of testing, for untreated rats and rats treated with SAN-Gly. Error bars represent one standard deviation.
Figure 2:
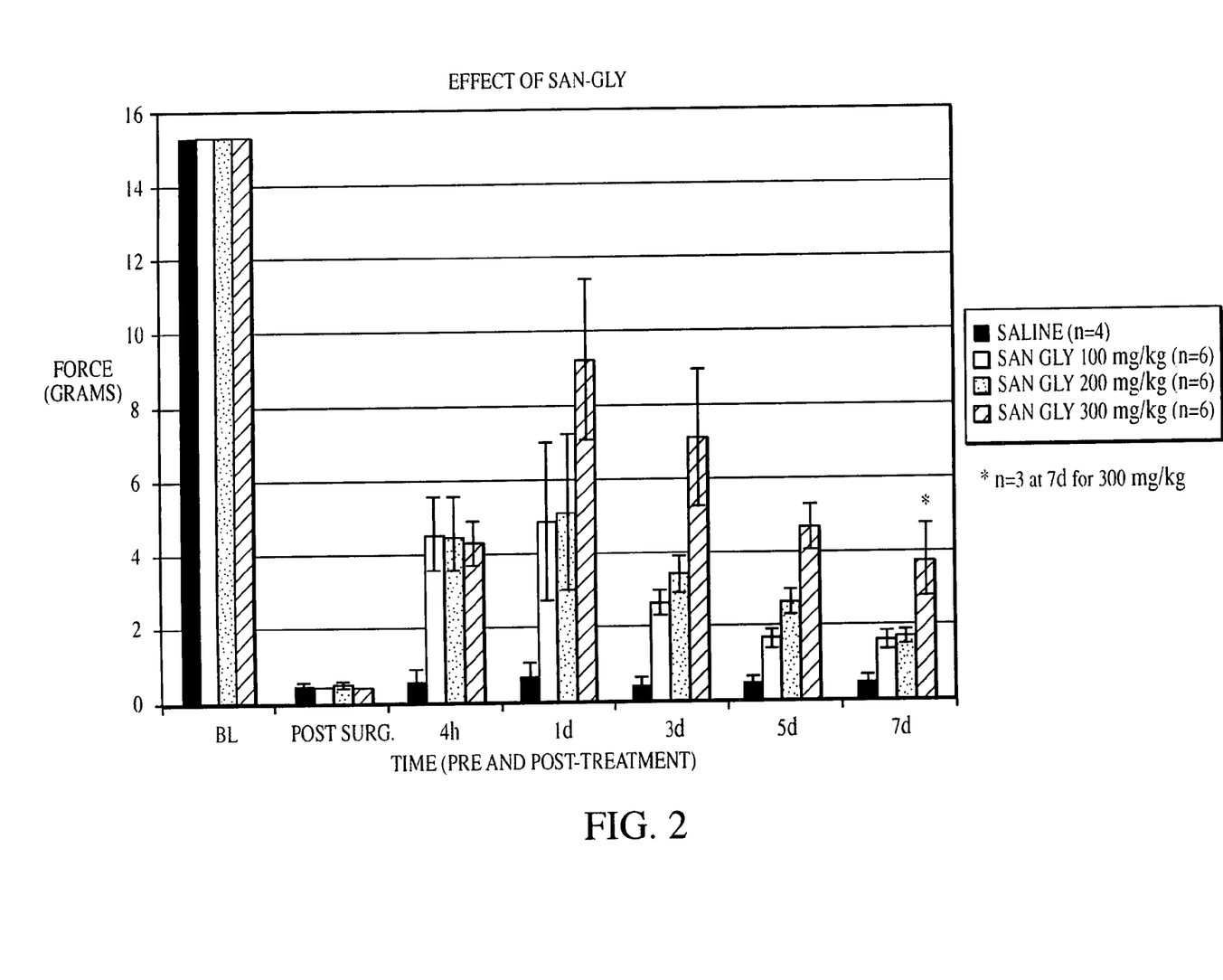
FIG. 2 is a bar graph of force in grams (high force correlates with high pain threshold) versus time of testing, for untreated rats and rats treated with SAN-Gly at 100 mg/Kg, 200 mg/Kg, and 300 mg/Kg. Error bars represent one standard deviation.

The results using both animal models were combined and summarized in FIG. 1. The single injection of SAN-Gly resulted in a 60% recovery towards baseline pain behavior, and this increased pain tolerance persisted for at least 7 days after surgery. Thus, SAN-Gly proved to be useful as an analgesic in two animal models of pain.

EXAMPLE 2

Electrophysiological recordings were done on 650 μm thick transverse slices of lumbar spinal cord (from spared-nerve injury animals) with attached L4 dorsal root that were perfused with ice cold Krebs' solution ([in mM]: NaCl 117, KCl 3.6, $CaCl_2$ 2.5, $MgCl_2$ 1.2, $NaH_2PO_4$ 1.2, $NaHCO_3$ 25 and glucose 11) saturated with 95% $O_2$ and 5% $CO_2$. To record primary afferent-evoked excitatory postsynaptic currents (EPSCs) from lamina II, whole cells were patch-clamped and then voltage-clamped at −70 mV. Orthodromicstimulation of L4 dorsal root was performed with a suction electrode attached to a constant current stimulator and graded intensity stimulation sufficient to recruit different afferent populations (Aβ, Aδ, and C-fibers) was used. Resistance of patch pipettes were 5–10 MW when filled with (in mM): $Cs_2SO_4$ 110, $CaCl_2$ 0.5, $MgCl_2$ 2, EGTA 5, HEPES 5, TEA 5, ATP-Mg salt 5. Currents were amplified (Axopatch 200A), filtered at 2 kHz, digitized at 5 kHz and analyzed using pCLAMP 6 (Axon Instruments). SAN-Gly was dissolved in ice cold KREBs and bath-applied at two concentrations (10 and 100 mM). It was observed in three out of five cells that 100 mM SAN-Gly increased the latency and reduced the amplitude of EPSCs, consistent with the hypothesis that it might play a role in inhibiting synaptic transmission in the dorsal horn. This effect was reversed upon washout of the drug. In addition, as expected, the same concentration of SAN had no effect. This example demonstrates that SAN-Gly and its derivatives are useful in treating neuropathic pain.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A method of providing pain relief, the method comprising
identifying a subject in need of pain relief; and
administering to the subject an amount of a compound of Formula II, or a salt thereof, effective to provide significant pain relief in the subject, Formula II wherein $R_1$ and $R_2$ are different from each other and represent —H or —OH, and R represents (1) an unsubstituted alkyl having one or two carbon atoms, or (2) —H.

2. The method of claim 1, wherein R has two carbon atoms.

3. A method of providing pain relief, the method comprising
identifying a subject in need of pain relief; and
administering to the subject an amount of a compound of Formula II, or a salt thereof, effective to provide significant pain relief in the subject, Formula II wherein $R_1$ and $R_2$ are different from each other and represent —H or —OH, and wherein R is —$COCH_2NH_2$.

4. The method of claim 3, wherein $R_1$ is —H and $R_2$ is —OH.

5. The method of claim 1, wherein $R_1$ is —H and $R_2$ is —OH.

6. The method of claim 1, wherein the pain is neuropathic pain.

7. The method of claim 6, wherein the pain is postherpetic neuralgia, phantom or amputation stump pain, diabetic neuropathy, acquired immune deficiency syndrome neuropathy, back pain, visceral pain, or chronic pancreatitic neuropathy.

8. The method of claim 1, wherein the pain is opioid-resistant.

9. The method of claim 1, wherein the subject is a mammal.

10. The method of claim 1, wherein the subject is a human.

11. The method of claim 1, wherein the compound is administered systemically.

12. The method of claim 1, wherein the compound is administered at a site of pain in the subject.

13. The method of claim 1, wherein the compound is administered via an implant.

14. The method of claim 13, wherein the implant provides slow release of the compound.

15. The method of claim 1, wherein the compound is administered intravenously.

16. The method of claim 1, wherein the amount administered is about 1 ng to 4 mg/m$^2$ body surface area.

17. The method of claim 1, wherein the amount administered is about 80 ng to 1 mg/m$^2$ patient body surface area.

18. The method of claim 1, wherein the amount administered is about 10 to 100 mg/kg body weight.

19. The method of claim 18, wherein the amount administered is about 100 mg/kg body weight.

20. The method of claim 1, wherein the compound is administered in an aqueous solution.

21. The method of claim 1 wherein neuropathic pain is selectively relieved over nociceptive pain.

22. The method of claim 3, wherein the pain is neuropathic pain.

23. The method of claim 22, wherein the pain is postherpetic neuralgia, phantom or amputation stump pain, diabetic neuropathy, acquired immune deficiency syndrome neuropathy, back pain, visceral pain, or chronic pancreatitic neuropathy.

24. The method of claim 3, wherein the pain is opioid-resistant.

25. The method of claim 3, wherein the subject is a mammal.

26. The method of claim 3, wherein the subject is a human.

27. The method of claim 3, wherein the compound is administered systemically.

28. The method of claim 3, wherein the compound is administered at a site of pain in the subject.

29. The method of claim 3, wherein the compound is administered via an implant.

30. The method of claim 29, wherein the implant provides slow release of the compound.

31. The method of claim 3, wherein the compound is administered intravenously.

32. The method of claim 3, wherein the amount administered is about 1 ng to 4 mg/m$^2$ body surface area.

33. The method of claim 3, wherein the amount administered is about 80 ng to 1 mg/m$^2$ patient body surface area.

34. The method of claim 3, wherein the amount administered is about 10 to 100 mg/kg body weight.

35. The method of claim 34, wherein the amount administered is about 100 mg/kg body weight.

36. The method of claim 3, wherein the compound is administered in an aqueous solution.

37. The method of claim 3, wherein neuropathic pain is selectively relieved over nociceptive pain.

\* \* \* \* \*

UNITED STATES PATENT AND TRADEMARK OFFICE
CERTIFICATE OF CORRECTION

PATENT NO. : 7,196,071 B2 Page 1 of 1
APPLICATION NO. : 10/380354
DATED : March 27, 2007
INVENTOR(S) : Borsook It is certified that error appears in the above-identified patent and that said Letters Patent is hereby corrected as shown below:

On the Title Page:
Item (*) Notice: Please correct "U.S.C. 154(b) by 286 days."
　　　　　　　　To read -- U.S.C. 154(b) by 623 days. --

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,196,071 B2  Page 1 of 1
APPLICATION NO. : 10/380354
DATED : March 27, 2007
INVENTOR(S) : David Borsook It is certified that error appears in the above-identified patent and that said Letters Patent is hereby corrected as shown below:

This certificate supersedes the Certificate of Correction issued April 27, 2010. The certificate should be vacated since request for patent term adjustment under 37 CFR 1.705(d) has been dismissed by the Office of Petitions. The Certificate of Correction should not have been issued for this patent and the term of this patent is reinstated to be extended or adjusted under 35 U. S. C. 154(b) by --286 days--.

Signed and Sealed this

Twenty-third Day of November, 2010

David J. Kappos
*Director of the United States Patent and Trademark Office*